(12) United States Patent
Flick

(10) Patent No.: US 11,129,419 B2
(45) Date of Patent: *Sep. 28, 2021

(54) AEROSOL GENERATING SYSTEM WITH MEANS FOR DISABLING CONSUMABLE

(71) Applicant: Philip Morris Products S.A., Neuchatel (CH)

(72) Inventor: Jean-Marc Flick, Pomy (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,832

(22) Filed: Mar. 30, 2020

(65) Prior Publication Data

US 2020/0232766 A1 Jul. 23, 2020

Related U.S. Application Data

(62) Division of application No. 16/030,469, filed on Jul. 9, 2018, now Pat. No. 10,655,938, which is a division
(Continued)

(30) Foreign Application Priority Data

Dec. 24, 2010 (EP) .................................... 10252236

(51) Int. Cl.
*A24F 47/00* (2020.01)
*A24F 40/53* (2020.01)
(Continued)

(52) U.S. Cl.
CPC .............. *A24F 40/53* (2020.01); *A24F 40/40* (2020.01); *A24F 40/50* (2020.01); *A61L 9/037* (2013.01);
(Continued)

(58) Field of Classification Search
None
See application file for complete search history.

(56) References Cited

U.S. PATENT DOCUMENTS 4,947,874 A    8/1990  Brooks et al.
5,060,671 A   10/1991  Counts et al.
(Continued)

FOREIGN PATENT DOCUMENTS

CN    2391624 Y    8/2000
CN    1633247 A    6/2005
(Continued)

OTHER PUBLICATIONS

Office Action dated Nov. 1, 2017 in Japanese Patent Application No. 2013-545408 (with English language translation), 9 pages.
(Continued)

*Primary Examiner* — Cynthia Szewczyk
(74) *Attorney, Agent, or Firm* — Oblon, McClelland, Maier & Neustadt, L.L.P.

(57) ABSTRACT

An aerosol-generating system is provided, including a storage portion configured to store an aerosol-forming substrate; an aerosol-generating element configured to generate an aerosol from the aerosol-forming substrate; a control circuitry in communication with the storage portion or the aerosol-generating element; and disabling means for rendering the storage portion inoperable in the aerosol-generating system in response to a disable signal from the control circuitry. There is also provided a method in an aerosol-generating system, including sending a disable signal from the control circuitry to the disabling component following a determination that an amount of the aerosol-substrate in the storage portion is below a threshold level or following a determination of a malfunction in the system.

8 Claims, 2 Drawing Sheets

Figure 1:
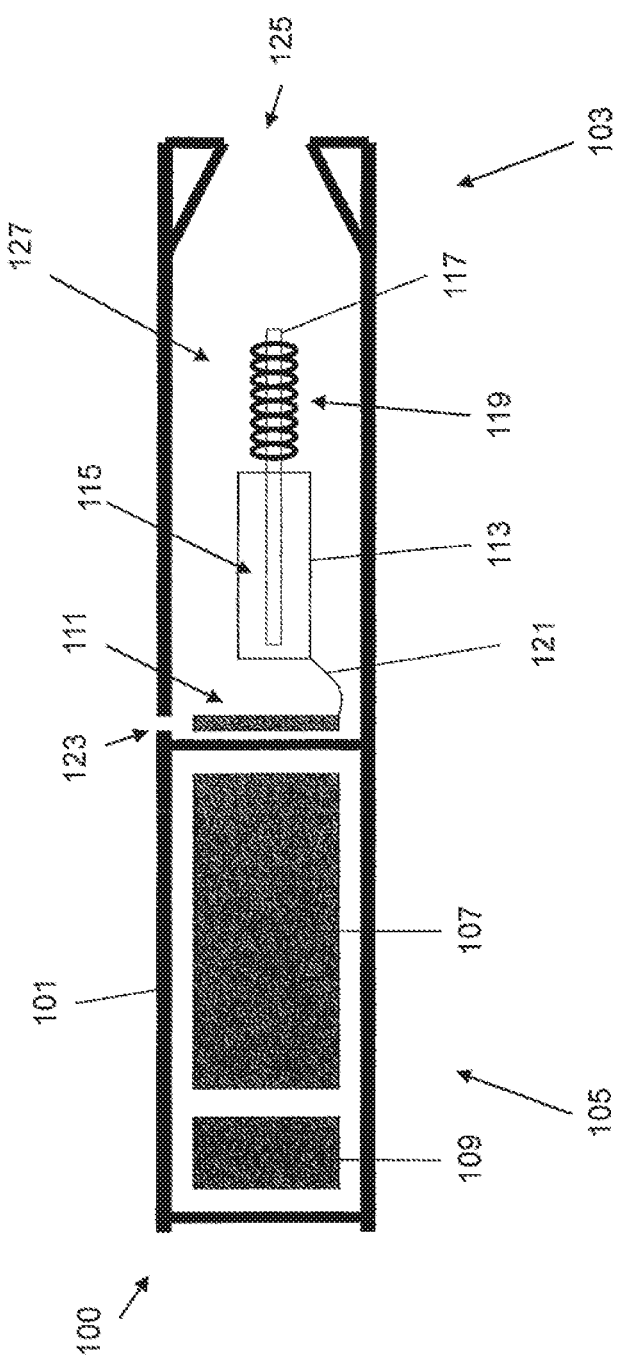

Related U.S. Application Data of application No. 13/996,707, filed as application No. PCT/EP2011/073793 on Dec. 22, 2011, now Pat. No. 10,045,561.

(51) Int. Cl.
*A61L 9/03* (2006.01)
*A24F 40/40* (2020.01)
*A24F 40/50* (2020.01)
*B63C 9/115* (2006.01)
*F41H 1/02* (2006.01)
*A24F 40/10* (2020.01)

(52) U.S. Cl.
CPC ............... *B63C 9/115* (2013.01); *F41H 1/02* (2013.01); *A24F 40/10* (2020.01); *A61L 2209/132* (2013.01); *A61L 2209/135* (2013.01)

(56) References Cited

U.S. PATENT DOCUMENTS

| | | |
|---|---|---|
| 5,095,921 A | 3/1992 | Losee et al. |
| 5,126,078 A | 6/1992 | Steiner et al. |
| 5,144,962 A | 9/1992 | Counts et al. |
| 6,234,167 B1 | 5/2001 | Cox et al. |
| 6,312,072 B1 | 11/2001 | Hough |
| 6,501,052 B2 | 12/2002 | Cox et al. |
| 6,766,220 B2 | 7/2004 | McRae et al. |
| 7,779,831 B1 | 8/2010 | Von Hollen et al. |
| 2002/0105099 A1 | 8/2002 | Warren |
| 2003/0140921 A1 | 7/2003 | Smith et al. |
| 2003/0154991 A1 | 8/2003 | Fournier et al. |
| 2005/0016550 A1 | 1/2005 | Katase |
| 2006/0047368 A1 | 3/2006 | Maharajh et al. |
| 2007/0008121 A1 | 1/2007 | Hart |
| 2007/0074734 A1 | 4/2007 | Braunshteyn et al. |
| 2008/0023464 A1 | 1/2008 | Otto et al. |
| 2010/0163063 A1 | 7/2010 | Fernando et al. |
| 2011/0226236 A1 | 9/2011 | Buchberger |
| 2011/0265806 A1 | 11/2011 | Alarcon |
| 2012/0234821 A1 | 9/2012 | Shimizu |

FOREIGN PATENT DOCUMENTS

| | | |
|---|---|---|
| CN | 200994936 Y | 12/2007 |
| CN | 201064183 Y | 5/2008 |
| CN | 201640457 U | 11/2010 |
| EP | 0 358 002 | 3/1990 |
| EP | 0 485 134 | 5/1992 |
| EP | 0 893 071 A1 | 1/1999 |
| EP | 1 211 628 A2 | 6/2002 |
| EP | 2 399 636 A1 | 12/2011 |
| EP | 2 466 116 A1 | 6/2012 |
| GB | 2 262 452 A | 6/1993 |
| GB | 2 263 068 A | 7/1993 |
| JP | 2-124081 | 5/1990 |
| JP | 2-165954 A | 6/1990 |
| JP | 3-232481 A | 10/1991 |
| JP | 9-289073 A | 11/1997 |
| JP | 11-89551 A | 4/1999 |
| JP | 2000-308672 A | 11/2000 |
| JP | 3258657 B | 12/2001 |
| JP | 2002-165882 | 6/2002 |
| JP | 2002-165882 A | 6/2002 |
| JP | 3392138 B2 | 1/2003 |
| JP | 2003-290356 A | 10/2003 |
| JP | 2004-97617 A | 4/2004 |
| JP | 2007-505644 | 3/2007 |
| JP | 3976345 | 9/2007 |
| JP | 2010-6344 A | 1/2010 |
| JP | 2010-112631 A | 5/2010 |
| JP | 2014-501106 A | 1/2014 |
| KR | 10-0178387 | 2/1999 |
| WO | WO 95/01137 | 1/1995 |
| WO | WO 97/48293 A1 | 12/1997 |
| WO | WO 2005/120614 A | 12/2005 |
| WO | WO 2007/078273 A1 | 7/2007 |
| WO | WO 2007/136795 A1 | 11/2007 |
| WO | WO 2009/086780 A1 | 7/2009 |
| WO | WO 2010/045671 A1 | 4/2010 |
| WO | WO 2012/027350 A2 | 3/2012 |

OTHER PUBLICATIONS

Eurasian Office Action dated Jun. 30, 2016 in Patent Application No. 201390953/31 (with English translation).
Office Action dated Aug. 6, 2018 in Indonesian Patent Application No. W00201303416 (with English translation).
Japanese Office Action dated Nov. 30, 2015 in Patent Application No. 2013-545408 (with English Translation).
Korean Office Action with English translation dated Feb. 21, 2018 in corresponding Korean Patent Application No. 2013-7016627, (14 pages).
International Search Report dated Apr. 27, 2012 in PCT/EP11/073793 filed Dec. 22, 2011.
Office Action dated May 19, 2017 in Australian Patent Application No. 2011347187.
Combined Chinese Office Action and Search Report dated Sep. 27, 2017 in Patent Application No. 201510850402.5 (with English language translation).
Japanese Office Action with Engligh translation dated Jun. 3, 2019 in corresponding Japanese Patent Application No. 2018-036727, (3 pages).
European Search Report dated Sep. 11, 2019 in corresponding European Patent Application No. 19168360.6, (10 pages).
Indian Office Action dated Feb. 25, 2019 in Indian Patent Application No. 5593/DELNP/2013 (with English translation), 7 pages.
Notice of Opposition dated Sep. 30, 2016 in EP 2 654 471 B1, (24 pages).
Statement of the Ground of Appeal dated May 29, 2016 in European Patent 2 654 471, (24 pages).
Korean Office Action dated May 30, 2019 in Patent Application No. 10-2013-7016627 (with English translation), 12 pages.
Japanese Office Action dated Mar. 8, 2021 in Japanese Patent Application No. 2020-079052 (with English translation), 4 pages.

AEROSOL GENERATING SYSTEM WITH MEANS FOR DISABLING CONSUMABLE

CROSS REFERENCE TO RELATED APPLICATION

This application is a divisional application of and claims the benefit of priority under 35 U.S.C. § 120 for U.S. Ser. No. 16/030,469, filed on Jul. 9, 2018, which is a divisional application of and claims the benefit of priority under 35 U.S.C. § 120 for U.S. Ser. No. 13/996,707, filed on Aug. 8, 2013, which is a National Stage application of PCT/EP2011/073793, filed on Dec. 22, 2011, and claims benefit of priority under 35 U.S.C. § 119 from EP 10 252 236.4, filed on Dec. 24, 2010, the entire contents of each of which are incorporated herein by reference.

The present invention relates to an aerosol generating system. In particular, the present invention relates to an aerosol generating system in which the aerosol-forming substrate is liquid and is contained in a liquid storage portion.

WO 2007/078273 discloses an electric smoking utensil. A liquid is stored in a container which communicates with a heater vaporiser, powered by a battery supply, via a series of small apertures. The heater is in the form of a spirally wound electric heater mounted on an electrically insulating support. In use, the heater is activated by the mouth of a user to switch on the battery power supply. Suction on a mouthpiece by the user causes air to be drawn through holes in the container, over the heater vaporiser, into the mouthpiece and subsequently into the mouth of a user.

The aerosol generating systems of the prior art, including the smoking system referred to above, do have a number of advantages, but there is still opportunity for improvement in the design, particularly concerning the handling of the liquid storage portion.

According to a first aspect of the invention, there is provided an aerosol generating system comprising:
a storage portion containing an aerosol-forming substrate;
an aerosol generating element for generating an aerosol from the aerosol-forming substrate;
control circuitry in communication with the storage portion or the aerosol generating element; and
disabling means for rendering the storage portion inoperable in the aerosol generating system in response to a disable signal from the control circuitry.

Preferably, the disabling means is part of the storage portion. Preferably the aerosol generating system is an electrically operated system. The aerosol generating element is preferably electrically operated. Preferably, the storage portion is separable from a main body of the aerosol generating system, and the control circuitry is arranged in the main body of the aerosol generating system.

It is advantageous to be able to automatically disable the storage portion for several reasons. If the storage portion is empty or nearly empty, or if there is a system malfunction, the system may not produce aerosol with the desired characteristics, for example, aerosol particle size or chemical composition. In addition, if the liquid storage portion is empty or nearly empty, disabling the storage portion is a means to inform the user the aerosol-forming substrate needs to be replaced. Also, automatically disabling the storage portion may be used to prevent, or at least make more difficult, the reuse of the storage portion refilled with inferior, inappropriate or even harmful substrate materials.

The aerosol generating system preferably further comprises a main body and the storage portion forms or is part of a consumable cartridge configured to couple to the main body. It is advantageous to be able to disable a consumable cartridge but to maintain a main body as a reusable part. The main body may include the more expensive components such as control circuitry and a user interface.

Preferably, the disabling means is an electrical component that is configured to be switched or damaged by the disable signal. Preferably, the component is an electrical fuse that can be blown by a sufficiently high current signal. Preferably the disable signal is a current sufficient to blow the fuse. However, other electrical components may be used such as a switch or transistor. However, other means for disabling the storage portion may be used. For example, the control circuitry may be configured to optically check the storage portion before the aerosol generating element can be activated and the disabling means may be an electrochromic material, or a thermochromic ink on the storage portion that is heated by a heater in response to a disable signal.

Alternatively, in cases where the storage portion is recognized or identified using logic circuitry (e.g. electric, electromagnetic or optic) by means of a unique identifier, the same circuitry can be used to write an 'invalidate bit' (flag bit) into the memory of that circuitry by which the storage portion is "disabled" and thus can not be used with the underlying aerosol generating system. However, in cases where the storage portion comprises such logic circuitry, the invalidate bit can even be stored on the storage portion itself, thus preventing its further use with another aerosol generating system.

The control circuitry is preferably configured to determine or estimate when an amount of aerosol-forming substrate in the storage portion is below a threshold amount, and to issue the disable signal when the amount of aerosol-forming substrate in the storage portion is determined or estimated to be below the threshold amount. The control circuitry may determine the amount of substrate in the storage portion by direct measurement, indirect measurement or by calculation. For example, the system may include means to directly measure the mass of the storage portion, such as balance. The control circuitry may be configured to calculate the mass of substrate consumed by monitoring the use of the system. For example, the control circuitry may calculate substrate consumption based on a number of times the aerosol generating element has been activated. Alternatively, the control circuitry may use a change in the behaviour of the system indicative of the storage portion becoming empty to estimate the amount of substrate remaining in the storage portion.

The threshold amount of liquid aerosol-forming substrate in the liquid storage portion may be an absolute amount or a relative amount, e.g. a percentage value.

If the amount of liquid aerosol-forming substrate has decreased, for example if the liquid storage portion is empty or nearly empty, insufficient liquid aerosol-forming substrate may be supplied to the aerosol generating element. In the case of a heater being used as the aerosol generating element, this may result in the temperature of the heater increasing. Thus, the temperature of the heater, as sensed by the temperature sensor may allow the electric circuitry to determine that the amount of liquid aerosol-forming substrate in the liquid storage portion has decreased to a predetermined threshold.

The control circuitry is preferably configured to issue the disable signal when the control circuitry has detected a malfunction in the system. For example, if a heater is used to generate aerosol, a temperature sensor may be used to detect any overheating of the heater or substrate. The temperature sensor is coupled to the control circuitry and the control circuitry issues a disable signal if the temperature sensed by the temperature sensor exceeds a first temperature threshold. This is advantageous as it allows the system to prevent the generation of undesirable or harmful aerosol constituents.

The aerosol-forming substrate preferably has physical properties, for example a boiling point, suitable for use in the aerosol generating system. The aerosol-forming substrate is preferably a liquid. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol.

Preferably the storage portion is configured such that the substrate in the storage portion is protected from ambient air and, in some embodiments light, so that the risk of degradation of the substrate is significantly reduced. Moreover, a high level of hygiene can be maintained.

The aerosol generating element is preferably a heater configured to heat the substrate. However, other aerosol generating elements can be used, such as a vibrating transducer.

The heater is preferably an electric heater. The electric heater may comprise a single electric heating element. Alternatively, the electric heater may comprise more than one heating element, for example two, or three, or four, or five, or six or more heating elements. The heating element or heating elements may be arranged appropriately so as to most effectively heat the liquid aerosol-forming substrate.

Preferably, the control circuitry is configured to issue a disable signal in response to a temperature or resistance measurement. More preferably, the control circuitry is configured to issue a disable signal in response to a determination that the temperature or resistance of a heating element has exceeded a predetermined threshold.

The electric heating element (or elements) preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company.

The electric heating element may take any suitable form. For example, the at least one electric heating element may take the form of a heating blade. Alternatively, the at least one electric heating element may take the form of a casing or substrate having different electro-conductive portions, or an electrically resistive metallic tube. The storage portion may incorporate a disposable heating element. Alternatively, one or more heating needles or rods that run through the aerosol-forming substrate may also be suitable. Alternatively, the electric heating element may comprise a flexible sheet of material. Other alternatives include a heating wire or filament, for example a Ni—Cr, platinum, tungsten or alloy wire, or a heating plate. Optionally, the heating element may be deposited in or on a rigid carrier material.

The heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The heater may heat the liquid aerosol-forming substrate by means of conduction. The heater may be at least partially in contact with the substrate. Alternatively, the heat from the heater may be conducted to the substrate by means of a heat conductive element.

Alternatively, the heater may transfer heat to the incoming ambient air that is drawn through the electrically operated aerosol generating system during use, which in turn heats the aerosol-forming substrate by convection. The ambient air may be heated before passing through the aerosol-forming substrate. Alternatively, the ambient air may be first drawn through the substrate and then heated.

Preferably, the aerosol forming substrate is a liquid at room temperature and the aerosol generating system further comprises a capillary wick for conveying the liquid aerosol-forming substrate from the storage portion to the aerosol generating element.

Preferably, the capillary wick is arranged to be in contact with liquid in the storage portion. Preferably, the capillary wick extends into the storage portion. In that case, in use, liquid is transferred from the storage portion to the electric heater (or other aerosol generating element) by capillary action in the capillary wick. In one embodiment, the capillary wick has a first end and a second end, the first end extending into the storage portion for contact with liquid therein and an electric heater being arranged to heat liquid in the second end. When the heater is activated, the liquid at the second end of the capillary wick is vaporized by the at least one heating element of the heater to form the supersaturated vapour. The supersaturated vapour is mixed with and carried in the air flow. During the flow, the vapour condenses to form the aerosol and the aerosol is carried towards the mouth of a user. The liquid aerosol-forming substrate has physical properties, including viscosity, which allow the liquid to be transported through the capillary wick by capillary action.

The capillary wick may have a fibrous or spongy structure. The capillary wick preferably comprises a bundle of capillaries. For example, the capillary wick may comprise a plurality of fibres or threads or other fine bore tubes. The fibres or threads may be generally aligned in the longitudinal direction of the aerosol generating system. Alternatively, the capillary wick may comprise sponge-like or foam-like material formed into a rod shape. The rod shape may extend along the longitudinal direction of the aerosol generating system. The structure of the wick forms a plurality of small bores or tubes, through which the liquid can be transported by capillary action. The capillary wick may comprise any suitable material or combination of materials. Examples of suitable materials are capillary materials, for example a sponge or foam material, ceramic- or graphite-based materials in the form of fibres or sintered powders, foamed metal or plastics material, a fibrous material, for example made of spinned or extruded fibres, such as cellulose acetate, polyester, or bonded polyolefin, polyethylene, terylene or polypropylene fibres, nylon fibres or ceramic. The capillary wick may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

Preferably, the aerosol generating element is in the form of a heating wire or filament encircling, and optionally supporting, the capillary wick. The capillary properties of the wick, combined with the properties of the liquid substrate, ensure that, during normal use when there is plenty of aerosol-forming substrate, the wick is always wet in the heating area.

The aerosol generating system may comprise a user display. In that case, the indication may comprise an indication on the user display. Alternatively, the indication may comprise an audible indication, or any other suitable type of indication for a user.

The aerosol generating system may further comprise an electric power supply. Preferably, the aerosol generating system comprises a housing. Preferably, the housing is elongate. If the aerosol generating includes a capillary wick, in use the longitudinal axis of the capillary wick and the longitudinal axis of the housing may be substantially parallel. The housing may comprise a shell and a mouthpiece. In that case, all the components may be contained in either the shell or the mouthpiece. In a preferred embodiment, the housing includes a removable consumable cartridge comprising the storage portion, the capillary wick and the heater. In that embodiment, those parts of the aerosol generating system may be removable from the housing as a single component.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating system is portable. The aerosol generating system may be a smoking system and may have a size comparable to a conventional cigar or cigarette. The smoking system may have a total length between approximately 30 mm and approximately 100 mm. The smoking system may have an external diameter between approximately 5 mm and approximately 13 mm.

Preferably, the electrically operated aerosol generating system is an electrically heated smoking system.

In a second aspect, the invention provides a cartridge for use in an aerosol generating system, the cartridge comprising an aerosol forming substrate; and disabling means for rendering the cartridge inoperable in the aerosol generating system, the disabling means configured to be activated by a signal from the aerosol generating system.

The aerosol forming substrate and disabling means may take any of the forms described in relation to the first aspect of the invention. The cartridge may include a storage portion for storing the aerosol-forming substrate and may include a capillary wick as described in relation to the first aspect of the invention. The cartridge may further include an aerosol generating element as described in relation to the first aspect of the invention. The cartridge may further include one or more of control circuitry, a power supply and a user interface as described in relation to the first aspect of the invention.

In a third aspect, the invention provides an aerosol generating device for use with a consumable cartridge, the consumable cartridge containing an aerosol-forming substrate and a disabling means configured to render the cartridge inoperable in the aerosol generating device in response to a disable signal, the aerosol generating system comprising:

control circuitry configured to issue a disable signal to the disabling means when the amount of aerosol-forming substrate in the storage portion is determined or estimated to be below a threshold amount or when a malfunction is detected.

The control circuitry may be configured as described in relation to the first aspect of the invention. The aerosol generating device may further include an aerosol generating element as described in relation to the first aspect of the invention. The cartridge may further include one or more of a power supply and a user interface as described in relation to the first aspect of the invention.

According to a fourth aspect of the invention, there is provided a method in an aerosol generating system comprising a storage portion for storing aerosol-forming substrate, an aerosol generating element for generating an aerosol from the aerosol-forming substrate, control circuitry in communication with the storage portion and disabling means associated with the storage portion for rendering the storage portion inoperable in the aerosol generating system in response to a disable signal from the control circuitry, the method comprising:

sending a disable signal from the control circuitry to the disabling means following a determination that an amount of the aerosol-substrate in the storage portion is below a threshold level or following a determination of a malfunction in the system.

According to a fifth aspect of the invention, there is provided electric circuitry for an aerosol generating system, the electric circuitry being arranged to perform the method of the second aspect of the invention.

According to a sixth aspect of the invention, there is provided a computer program which, when run on programmable electric circuitry for an aerosol generating system, causes the programmable electric circuitry to perform the method of the second aspect of the invention.

Features described in relation to the aerosol generating system of the invention may also be applicable to the method of the invention. And, features described in relation to the method of the invention may also be applicable to the aerosol generating system of the invention.

Figure 2:
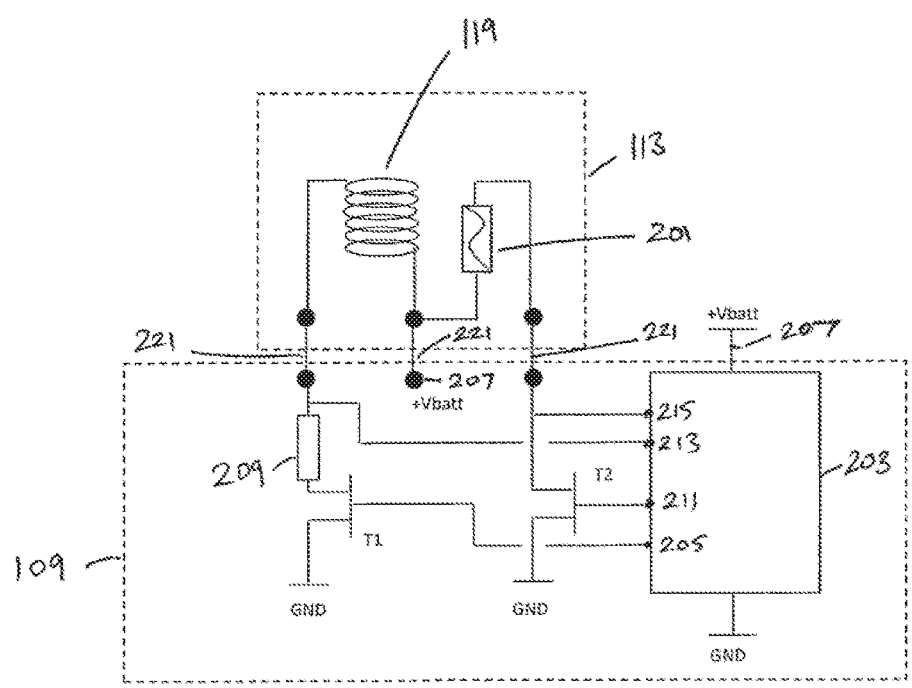

The invention will be further described, by way of example only, with reference to the accompanying drawings, of which:

FIG. 1 shows one example of an electrically operated aerosol generating system having a liquid storage portion; and FIG. 2 is a schematic illustration of a disabling mechanism suitable for use in a system as shown in FIG. 1.

FIG. 1 shows one example of an electrically operated aerosol generating system having a liquid storage portion. In FIG. 1, the system is a smoking system. The smoking system 100 of FIG. 1 comprises a housing 101 having a mouthpiece end 103 and a body end 105. In the body end, there is provided an electric power supply in the form of battery 107 and electric control circuitry 109. A puff detection system 111 is also provided in cooperation with the electric control circuitry 109. In the mouthpiece end, there is provided a liquid storage portion in the form of cartridge 113 containing liquid 115, a capillary wick 117 and a heater 119. Note that the heater is only shown schematically in FIG. 1. In the exemplary embodiment shown in FIG. 1, one end of capillary wick 117 extends into cartridge 113 and the other end of capillary wick 117 is surrounded by the heater 119. The heater is connected to the electric control circuitry via connections 121, which may pass along the outside of cartridge 113 (not shown in FIG. 1). The housing 101 also includes an air inlet 123, an air outlet 125 at the mouthpiece end, and an aerosol-forming chamber 127.

In use, operation is as follows. Liquid 115 is conveyed by capillary action from the cartridge 113 from the end of the wick 117 which extends into the cartridge to the other end of the wick which is surrounded by heater 119. When a user draws on the aerosol generating system at the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action".) The supersaturated vapour created is mixed with and carried in the air flow from the air inlet 123. In the aerosol-forming chamber 127, the vapour condenses to form an inhalable aerosol, which is carried towards the outlet 125 and into the mouth of the user.

In the embodiment shown in FIG. 1, the electric control circuitry 109 and puff detection system 111 are preferably programmable. The electric control circuitry 109 and puff detection system 111 can be used to manage operation of the aerosol generating system. This assists with control of the particle size in the aerosol.

FIG. 1 shows one example of an electrically operated aerosol generating system according to the present invention. Many other examples are possible, however. In addition, note that FIG. 1 is schematic in nature. In particular, the components shown are not to scale either individually or relative to one another. The aerosol generating system needs to include or receive an aerosol-forming substrate. The aerosol generating system requires some sort of aerosol generating element, such as a heater or vibrating transducer, for generating aerosol from the aerosol-forming substrate. Finally, the aerosol generating system requires control circuitry for disabling the system. This will be described below with reference to FIG. 2. For example, the system need not be a smoking system. A puff detection system need not be provided. Instead, the system could operate by manual activation, for example the user operating a switch when a puff is taken. For example, the overall shape and size of the housing could be altered. Moreover, the system may not include a capillary wick.

However, in a preferred embodiment, the system does include a capillary wick for conveying liquid substrate from a storage portion to at least one heating element. The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heater. Preferably, the heater comprises at least one heating wire or filament extending around the capillary wick.

The aerosol generating system of the invention includes control circuitry that is operable to disable the cartridge 113. This may be done for several reasons. In a preferred embodiment the control circuitry is configured for determining an amount of aerosol-forming substrate in the storage portion. When the liquid storage portion is determined to be empty or nearly empty, the control circuitry 109 disables the cartridge 113. This is primarily because if the storage portion is nearly empty, insufficient liquid aerosol-forming substrate may be supplied to the heater. This may mean that the aerosol created and inhaled by the user does not have the desired properties, for example, aerosol particle size. This may result in a poor experience for the user. In addition, it is advantageous to provide a mechanism whereby the user can be informed that the liquid storage portion is empty or nearly empty. Then the user can prepare to replace storage portion. Disabling empty cartridges also provides for user safety. There is a danger that cartridges could be refilled with inferior and possibly dangerous substances. But by disabling the cartridges in a permanent manner they cannot be refilled and reused.

FIG. 2 illustrates one embodiment of a disabling system that can be employed in a system as described with reference to FIG. 1. The disabling system of FIG. 2 has two parts. One part is held in the consumable cartridge 113 and the other part is held in the control circuitry 109. An electrical fuse 201 is located in the consumable. A connection port of three contacts 221 is used for interfacing the consumable storage portion 113 and the main body of the device 101. The consumable part contains the heater element 119. The power supplied to the heating element 119, which is in the form of a modulated signal, is controlled by the digital output 205 on the microcontroller 203 and via the transistor T1. The positive battery electrode 207 is connected to the other leg of the heating element 119 and the electrical fuse 201.

In the embodiment shown in FIG. 2 a determination that the cartridge 113 is nearly empty is made by monitoring the temperature of the heating element 119. If the cartridge is nearly empty, insufficient liquid aerosol-forming substrate is supplied to the heater through the wick. This results in the temperature of the heater increasing, as less energy is used to vaporise vaporising the substrate. Thus, the temperature of the heater allows the control circuitry to determine that the amount of liquid aerosol-forming substrate in the liquid storage portion has decreased to a predetermined threshold. Once the critical temperature is reached, the consumable is disabled to avoid a consumable violation by the consumer like the refilling of the cartridge. Disabling also provides the consumer with an indication that the consumable needs to be replaced. Disabling the consumable also prevents the generation of harmful constituents formed by an excess of heat.

The measurement of the temperature of the heating element is based on the calculation of the current passing through the resistance 209. This is determined from the signal to input 213 and on the voltage of the battery converted into digital values via two analogue inputs on the microcontroller. As the temperature of the heating element increases, so does its resistance. The relationship between resistance and temperature for the heating element can be programmed or stored in the microcontroller. When the microcontroller determines that the critical temperature has been reached, the microcontroller activates digital output 211 connected to the transistor T2, which blows the electrical fuse 201. After this operation each time the user draws on the device, the microcontroller 203 checks the validity of the fuse 201 via a consumable enable line 215 and if the connection is lost then the device will not operate. When the consumable is replaced by a new one, with an intact fuse, the system returns to normal operating mode.

It should be apparent that other means to disable the cartridge are possible and other circuit configurations possible when using a fuse or other switchable or breakable electronic component. For example a dedicated temperature sensor may be connected to the microcontroller positioned to detect the temperature of the heater element.

The control circuitry may be configured to advise the user when the control circuitry has determined that the amount of liquid in the liquid storage portion has decreased to a first threshold, and the cartridge disabled when the control circuitry has determined that the amount of liquid in the liquid storage portion has decreased to a second threshold. For example, if the aerosol generating system includes a user display, it may be indicated on the user display that the liquid storage portion is empty or nearly empty and an estimate of the number of remaining puffs before disabling will occur may be provided. Alternatively or additionally, an audible sound may indicate to the user that the liquid storage portion is empty or nearly empty. Alternative methods of indicating to the user that the liquid storage portion is empty or nearly empty are, of course, possible. An advantage of advising the user is that the user is then able to prepare to replace the liquid storage portion.

The present invention provides a system and method for rendering a consumable cartridge inoperable in an aerosol generating system. This has safety benefits as well as providing benefits in terms of user experience and convenience. Although one particular embodiment has been described, there are a number of ways of disabling the consumable cartridge and a number of conditions under which the disabling means may be activated that fall within the scope of the invention.

The invention claimed is:

1. An aerosol-generating system, comprising:
   a storage portion configured to store an aerosol-forming substrate;
   an aerosol-generating element configured to generate an aerosol from the aerosol-forming substrate;
   a control circuitry in communication with the storage portion or the aerosol-generating element; and
   disabling means for rendering the storage portion inoperable in the aerosol-generating system in response to a disable signal from the control circuitry,
   wherein the disabling means is a component that is configured to be switched or damaged by the disable signal to render the storage portion inoperable in a permanent manner, and
   wherein the aerosol-generating system is an electrically operated smoking system.

2. The aerosol-generating system according to claim 1, further comprising a main body, wherein the storage portion is a consumable cartridge configured to couple to the main body.

3. The aerosol-generating system according to claim 2, wherein the control circuitry is disposed in the main body of the aerosol-generating system.

4. The aerosol-generating system according to claim 1, wherein the component is an electrical fuse.

5. The aerosol-generating system according to claim 1, wherein the component is an electrical switch or digital information interacting with the control circuitry and representing an enable/disable state for the storage portion.

6. The aerosol-generating system according to claim 1, wherein the control circuitry is configured to issue the disable signal when the control circuitry has detected a malfunction in the aerosol-generating system.

7. The aerosol-generating system according to claim 1, wherein the aerosol-generating element configured to generate the aerosol from the aerosol-forming substrate is a heater configured to heat the aerosol-forming substrate.

8. A method in an electrically operated smoking system comprising a storage portion configured to store an aerosol-forming substrate, an aerosol-generating element configured to generate an aerosol from the aerosol-forming substrate, control circuitry in communication with the storage portion, and disabling means associated with the storage portion configured to render the storage portion inoperable in the electrically operated smoking system in response to a disable signal from the control circuitry, wherein the disabling means is a component that is configured to be switched or damaged by the disable signal to render the storage portion inoperable in a permanent manner, the method comprising:
   sending a disable signal from the control circuitry to the disabling means; and
   switching or damaging the disabling means by the disable signal to render the storage portion inoperable in a permanent manner.

\* \* \* \* \*